United States Patent [19]
Jurd

[11] 3,993,782
[45] Nov. 23, 1976

[54] REPELLENTS FOR THE CONFUSED FLOUR BEETLE

[75] Inventor: Leonard Jurd, Berkeley, Calif.

[73] Assignee: The United States of America as represented by the Secretary of Agriculture, Washington, D.C.

[22] Filed: Aug. 14, 1975

[21] Appl. No.: 604,854

[52] U.S. Cl. .......................... 424/346; 424/DIG. 10
[51] Int. Cl.$^2$ ............................................. A01N 9/26
[58] Field of Search ..................... 424/346, DIG. 10

[56] References Cited
UNITED STATES PATENTS 3,257,273   6/1966   Shambaugh et al. ............... 424/346
3,775,541   11/1973   Jurd et al. ........................... 424/346

OTHER PUBLICATIONS

Chemical Abstracts 63:15381h (1965).

*Primary Examiner*—Leonard Schenkman
*Attorney, Agent, or Firm*—M. Howard Silverstein; David G. McConnell; William Takacs

[57]   ABSTRACT

Alkyl-substituted 2-benzylphenols are disclosed to be useful for repelling the confused flour beetle (*Tribolium confusum*).

12 Claims, No Drawings

REPELLENTS FOR THE CONFUSED FLOUR BEETLE

DESCRIPTION OF THE INVENTION

The invention relates to and has among its objects the provision of novel methods for controlling insect infestations, particularly by repelling the insects. Further objects of the invention will be evident from the following description wherein parts and percentages are by weight unless otherwise specified.

The symbol $\phi$ is used herein to represent the phenyl

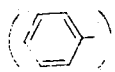

group.

The confused flour beetle (*Tribolium confusum*) is only one of many insects which prey on grain and grain products. It is, however, the most abundant and most injurious insect pest in flour mills in the United States.

Control of the confused flour beetle may be accomplished in several ways. For example, grain and grain products can be fumigated with such materials as hydrogen cyanide, ethylene oxide, ethyl formate, methyl formate, carbon disulphide, chlorinated hydrocarbons, and chloropicrin. Fumigation, however, has several disadvantages, particularly in the area of dispersion and toxicity of the fumigant. Another method of control is the use of insecticides which are not volatile. This approach also possesses disadvantages in that it can potentially cause harm to humans, warm-blooded animals, and useful insects (bees, for instance).

A third means of control is the use of repellents—compounds which do not kill the beetles but simply deter them from approaching and infesting the grain. Repellents have several advantages over fumigants or other insecticides. First of all, repellents need only be situated in strategic locations near the grain; application to the grain itself is not necessary. Consequently, the grain does not become contaminated with any material which might be deleterious to the grain or to the consumer thereof. Secondly, the success of fumigation depends on how well the fumigant can penetrate the substance treated. No such requirement is involved in the use of a repellent. Third, the use of fumigants requires that the treated grain be maintained under gas-tight conditions, whereas the use of repellents does not involve such container problems. In addition, repellents have an advantage over contact insecticides in that repellent compounds generally are non-toxic, not only to the confused flour beetle, but also to humans, animals, and other insects. A disadvantage in the use of known repellents for the confused flour beetle—for instance, pyrethrins and piperonyl butoxide—is that they are expensive.

In accordance with the invention, it has been found that certain compounds have the property of repelling the confused flour beetle, and therefore these compounds are useful as repellents to protect grain and grain products from infestation by this insect.

The repellent compounds of the invention are mono-alkyl-2-benzylphenols and di-alkyl-2-benzylphenols, which have the structure

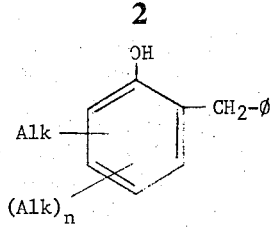

wherein each Alk is an alkyl radical containing from 1 to 10 carbon atoms, and $n$ is 0 or 1.

The compounds of the invention have the advantage that they are not only effective to repel the confused flour beetle, but also they are inexpensive. Another important advantage of the compounds of the invention is that they have low volatility. Thus, when the compounds are applied to an area, confused flour beetles will continue to be repelled from the area for months after the initial application.

In a practice of the invention the repellents are used in the same manner in which known repellents are employed. Basically, the desired repellent effect is attained by applying the compounds to or near the locus which is to be protected from infestation. For example, in protecting grain from infestation the compounds are applied to an area in close proximity to the grain. The concentration required to achieve the desired repellent effect will vary depending on the particular compound selected. In any particular case the appropriate amount to use can be readily determined by pilot tests well-known to entomologists. In many instances good results have been attained where the compounds are applied in a concentration of about 0.25 to 2 grams per sq. meter.

It is within the compass of the invention to incorporate the repellents in packaging materials such as paper, cardboard, cloth, etc. Grain or grain products packaged in such treated containers can be stored for long periods without infestation by the confused flour beetle.

EXAMPLE

The invention is further demonstrated by the following illustrative example.

Strips of aluminum foil (4 × 16 inches) were laminated to 40-lb. kraft paper. Some of the strips were treated on the paper side with acetone solutions of the candidate repellents. The solutions were applied with a Gardner automatic blade applicator to provide concentrations of the repellents of 0.25, 1, and 2 grams per square meter, respectively. Some of the strips were left untreated. Each of the above strips was cut into two 8-inch pieces. A treated strip was joined edge-to-edge lengthwise with an untreated strip by means of cellulose tape applied on the aluminum foil side. For each test (that is, each candidate compound at each concentration), two such test surfaces were prepared. They were placed on a work table with the paper side up. On each test surface, two glass cylinders (2.5 cm. high × 6.4 cm. inside diameter) were placed in such a way as to provide test arenas composed of equal areas of treated and untreated paper. Thus for each test, a total of four such test arenas (two each on two test surfaces) containing treated and untreated paper were prepared.

After 2 weeks had elapsed, 10 confused flour beetle adults were placed in each of the test arenas. The number of beetles on the treated half and on the untreated half of each arena was recorded at 9 A.M. and 3 P.M. for 5 consecutive days and the averages were determined.

Two months after preparation of the test arenas, 10 new confused flour beetle adults were placed in each of the test arenas. The number of beetles on the treated and untreated half of each arena was again recorded at 9 A.M. and 3 P.M. over a 5-day period.

The averages obtained in the above experiments were converted to percent repellency by doubling the difference between the percentage of insects counted on the untreated half and the 50% distribution obtained when only untreated paper was used. For example, if the average distribution in the treated-untreated test arenas was 20 and 80%, respectively, then the percent repellency would be determined as follows:

2 × [% (untreated half) minus 50% (random distribution)] or 2 × (80 − 50) = 60% repellency The compounds tested and the results obtained are summarized below. For purpose of comparison, a standard confused flour beetle repellent was also tested in the same manner. The standard employed was a mixture of pyrethrins and piperonyl butoxide applied at a concentration of 0.05 grams per sq. meter (pyrethrins) and 0.5 grams per sq. meter (piperonyl butoxide).

| Repellent | Concentration, g./sq. m. | Repellency, % 2 wks. | 2 months |
|---|---|---|---|
| 4-ethyl-2-benzylphenol | 0.25 | 59 | 58 |
| " | 1.0 | 94 | 80 |
| " | 2.0 | 91 | 90 |
| 4-t-butyl-2-benzylphenol | 0.25 | 66 | 46 |
| " | 1.0 | 88 | 74 |
| " | 2.0 | 91 | 63 |
| 4-methyl-6-t-butyl-2-benzylphenol | 1.0 | 76 | 61 |
| 4-nonyl-2-benzylphenol | 2.0 | 64 | 56 |
| pyrethrins/piperonyl butoxide | .05/0.5 | 63 | 38 |

Having thus described the invention, what is claimed is:

1. A method for repelling the confused flour beetle (*Tribolium confusum*), which comprises
    exposing said beetle to a repellent amount of a compound of the structure

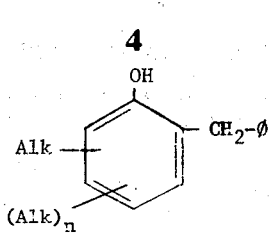

wherein each Alk is an alkyl radical containing from 1 to 10 carbon atoms and $n$ is 0 or 1.

2. The method of claim 1 wherein the beetle is repelled from a locus and the compound is applied to the locus.

3. The method of claim 1 wherein the compound is 4-ethyl-2-benzylphenol.

4. The method of claim 1 wherein the compound is 4-t-butyl-2-benzylphenol.

5. The method of claim 1 wherein the compound is 4-methyl-6-t-butyl-2-benzylphenol.

6. The method of claim 1 wherein the compound is 4-nonyl-2-benzylphenol.

7. A method for combatting an infestation of the confused flour beetle (*Tribolium confusum*), which comprises
    distributing on the infested area a repellent amount of a compound of the structure

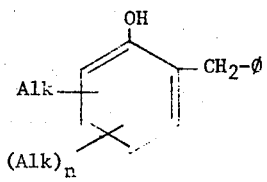

wherein each Alk is an alkyl radical containing 1 to 10 carbon atoms, and $n$ is 0 or 1.

8. The method of claim 7 wherein the infestation combatted is in grain or grain products and the compound is applied to an area in close proximity to the grain or grain product.

9. The method of claim 7 wherein the compound is 4-ethyl-2-benzylphenol.

10. The method of claim 7 wherein the compound is 4-t-butyl-2-benzylphenol.

11. The method of claim 7 wherein the compound is 4-methyl-6-t-butyl-2-benzylphenol.

12. The method of claim 7 wherein the compound is 4-nonyl-2-benzylphenol.

* * * * *